(12) United States Patent
Kok et al.

(10) Patent No.: US 9,849,105 B2
(45) Date of Patent: Dec. 26, 2017

(54) ACTIVE FORMULATION FOR USE IN FEED PRODUCTS

(75) Inventors: Symone Kok, Gorinchem (NL); Nikolaos Vogiatzis, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 14/131,216

(22) PCT Filed: Jul. 3, 2012

(86) PCT No.: PCT/EP2012/062926
§ 371 (c)(1),
(2), (4) Date: Feb. 12, 2014

(87) PCT Pub. No.: WO2013/007558
PCT Pub. Date: Jan. 17, 2013

(65) Prior Publication Data
US 2014/0161864 A1   Jun. 12, 2014

Related U.S. Application Data

(60) Provisional application No. 61/505,810, filed on Jul. 8, 2011.

(30) Foreign Application Priority Data

Jul. 8, 2011 (EP) ..................................... 11173177

(51) Int. Cl.
| | | |
|---|---|---|
| A61K 9/14 | (2006.01) |
| A61K 31/215 | (2006.01) |
| A23K 1/175 | (2006.01) |
| A61K 31/23 | (2006.01) |
| A61K 9/16 | (2006.01) |
| A23K 40/10 | (2016.01) |
| A23K 20/105 | (2016.01) |
| A23K 20/158 | (2016.01) |
| A23K 20/24 | (2016.01) |
| A23K 50/75 | (2016.01) |

(52) U.S. Cl.
CPC ............ *A61K 31/23* (2013.01); *A23K 20/105* (2016.05); *A23K 20/158* (2016.05); *A23K 20/24* (2016.05); *A23K 40/10* (2016.05); *A23K 50/75* (2016.05); *A61K 9/167* (2013.01)

(58) Field of Classification Search
CPC ........ A61K 31/23; A61K 9/167; A23K 1/164; A23K 1/002; A23K 1/1609; A23K 1/1753; A23K 1/1826; A23K 20/158; A23K 20/105; A23K 20/24; A23K 40/10; A23K 50/75
See application file for complete search history.

(56) References Cited

U.S. PATENT DOCUMENTS

| | | | | |
|---|---|---|---|---|
| 3,081,154 A * | 3/1963 | Acker | .................... | C01B 33/18 502/232 |
| 3,284,209 A | 11/1966 | Kelley | | |
| 5,002,780 A | 3/1991 | Bakta et al. | | |
| 5,270,027 A * | 12/1993 | Balducci | ................. | C01B 33/16 423/338 |
| 8,754,054 B2 * | 6/2014 | Carr | ..................... | A61K 31/704 514/42 |
| 2005/0233074 A1* | 10/2005 | Dalziel | ................. | A61K 9/143 427/233 |
| 2008/0111269 A1 | 5/2008 | Politi et al. | | |
| 2008/0293955 A1 | 11/2008 | Ruhle et al. | | |
| 2012/0160944 A1* | 6/2012 | Dodd | ..................... | A01N 25/12 241/30 |

FOREIGN PATENT DOCUMENTS

| | | |
|---|---|---|
| CN | 101212956 A | 7/2008 |
| CN | 101828584 A | 9/2010 |
| CN | 101973737 A | 2/2011 |
| CN | 101973740 A | 2/2011 |
| CN | 101973742 A | 2/2011 |
| CN | 101973743 A | 2/2011 |
| CN | 101973744 A | 2/2011 |

(Continued)

OTHER PUBLICATIONS

Teunou et al., Characterization of food powder flowability, 1999, Journal of Food Engineering, 39:31-37.*
Teunou et al., Characterization of food powder flowability, J. of Food Engineering, 1999, 39:31-27.*
Petrovic et al., On the Particles Size Distributions of Diatomaceous Earth and Perlite Granulations, Strojniski vestnik—Journal of Mechanical Engineering, 2011, 57(11):843-850.*
"Diatomaceous earth", Wikipedia [online], 1960-2013 [retrieved Sep. 11, 2015] Retrieved from the Internet: <URL: http://en.wikipedia-org/sedimentary_rock>.*
"Hausner ratio", Wikipedia [online], [retrieved Apr. 2, 2015] Retrieved from the Internet: <URL: http://en.wikipedia.org/wiki/Hausner_ratio>.*

(Continued)

*Primary Examiner* — Abigail Vanhorn
(74) *Attorney, Agent, or Firm* — Oliff PLC

(57) ABSTRACT

Invention pertains to a free-flowing particulate powder including 2-90 wt. % of an active compound on a carrier, wherein the carrier has a D(v,0.1) of at least 100 microns, with the active compound being selected from lactylate in accordance with formula (1), Formula (1): R2-COO—[—CH(CH3)-COO]n-R1 or a Na, K, Ca, Mg, Fe(II), Zn, NH4, or Cu(II) salt thereof, a glycolylate of formula (2), Formula (2): R2-COO—[—CH2-COO]n-R1 or a Na, K, Ca, Mg, Fe(II), Zn, NH4, or Cu(II) salt thereof a lactate ester of formula (3), Formula (3): HO—CH(CH3)-COO—R2 and/or a glycolic acid ester of formula (4), Formula (4): HO—CH2-COO—R2 wherein in the above formulae R1 is selected from H, n stands for an integer with a value of 1-10, and R2 stands for a C1-C35 alkyl or alkenyl chain which may be branched or unbranched. The powder allows easy provision of the active compound to feed compositions.

17 Claims, 1 Drawing Sheet

(56) References Cited

FOREIGN PATENT DOCUMENTS

| | | | |
|---|---|---|---|
| EP | 1 483 975 A1 | 12/2004 | |
| JP | H04-214801 A | 8/1992 | |
| JP | 2009270130 A | 11/2009 | |
| WO | 2007003425 A2 | 1/2007 | |
| WO | WO2007003425 A2 * | 1/2007 | |
| WO | WO 2009/092787 A1 | 7/2009 | |
| WO | WO2009092787 A1 * | 7/2009 | ............. A61K 31/23 |
| WO | WO 2011/026796 A1 | 3/2011 | |

OTHER PUBLICATIONS

Teunou et al., "Characterization of food powder flowability," 1999; J. of Food Engineering, 39:31-37.*

"Hausner ratio", Wikipedia [online], [retrieved Apr. 2, 2015], Retrieved from the Internet: <URL: http://en.wikipedia-org/wiki/Hausner_ratio>.*

Petrovic et al., "On the Particles Size Distributions of Diatomaceous Earth and Perlite Granulations," 2011; Strojniski-vestnik-Journal of Mechanical Engineering, 57(11):843-850.*

"Diatomaceous earth," Wikipedia [online], 1960-2013, [retrieved Sep. 11, 2016] Retrieved from the Internet: <URL: http://en.wikipedia-org/wiki/sedimentary_rock>.*

Terence Allen, "Surface Area and Pore Size Determination," 1997; Chapman & Hall, New York; Particle Size Measurement, vol. 2, pp. 47-57.*

Sipernat.com, SIPERNAT Specialty Silica for Purifiaction of Biodiesel Technical Information 1402, obtained online at: http://www.sipernat.com/sites/lists/IM/Documents/TI-1402-SIPERNAT-Specialty-Silica-for-Purification-of-Biodiesel-EN.pdf, downloaded on Oct. 20, 2016.*

Sipernat.com, Products: Sipernat 22, Sipernat 2200 and Sipernat 50, obtained online at: http://www.sipernat.com/product/sipernat/en/products/hydrophilic-silica/pages/default.aspx, downloaded on Oct. 20, 2016.*

Abdullah et al., Powder Technology, 1999, 102, 151-165.*

Mar. 10, 2016 Notice of the Reasons for Rejection issued in Japanese Application No. 2014-517771.

Lensing et al., "Efficacy of a Lactylate on Production Performance and Intestinal Health of Broilers During a Subclinical Clostridium Perfringens Infection," *Poultry Science*, vol. 89, 2010, pp. 2401-2409.

Teunou et al., "Characterisation of Food Powder Flowability," *Journal of Food Engineering*, vol. 39, 1999, pp. 31-37.

International Search Report issued in International Patent Application No. PCT/EP2012/062926 dated Feb. 8, 2013.

Apr. 5, 2016 Communication issued in European Application No. 12730585.2.

Nov. 24, 2016 Office Action issued in Japanese Patent Application No. 2014-517771.

Dupre Minerals. "Vermiculite Animal Feed". Retrieved from the Internet:URL;https://web.archive.org/web/20110405021615/http://www.depreminerals.com/en/vermiculite/applications/animal-feed, 1 page, Apr. 5, 2011.

Mohamed Kehal, et al. "The Trapping of B from Water by Exfoliated and Functionalized Vermiculite", Clays and Clay Minerals, vol. 56, No. 4, pp. 453-460, Aug. 1, 2008.

Oct. 31, 2016 Office Action issued in European Patent Application No. 12730585.2.

Apr. 29, 2016 Office Action issued in Russian Application No. 2014102671/13(004157).

* cited by examiner

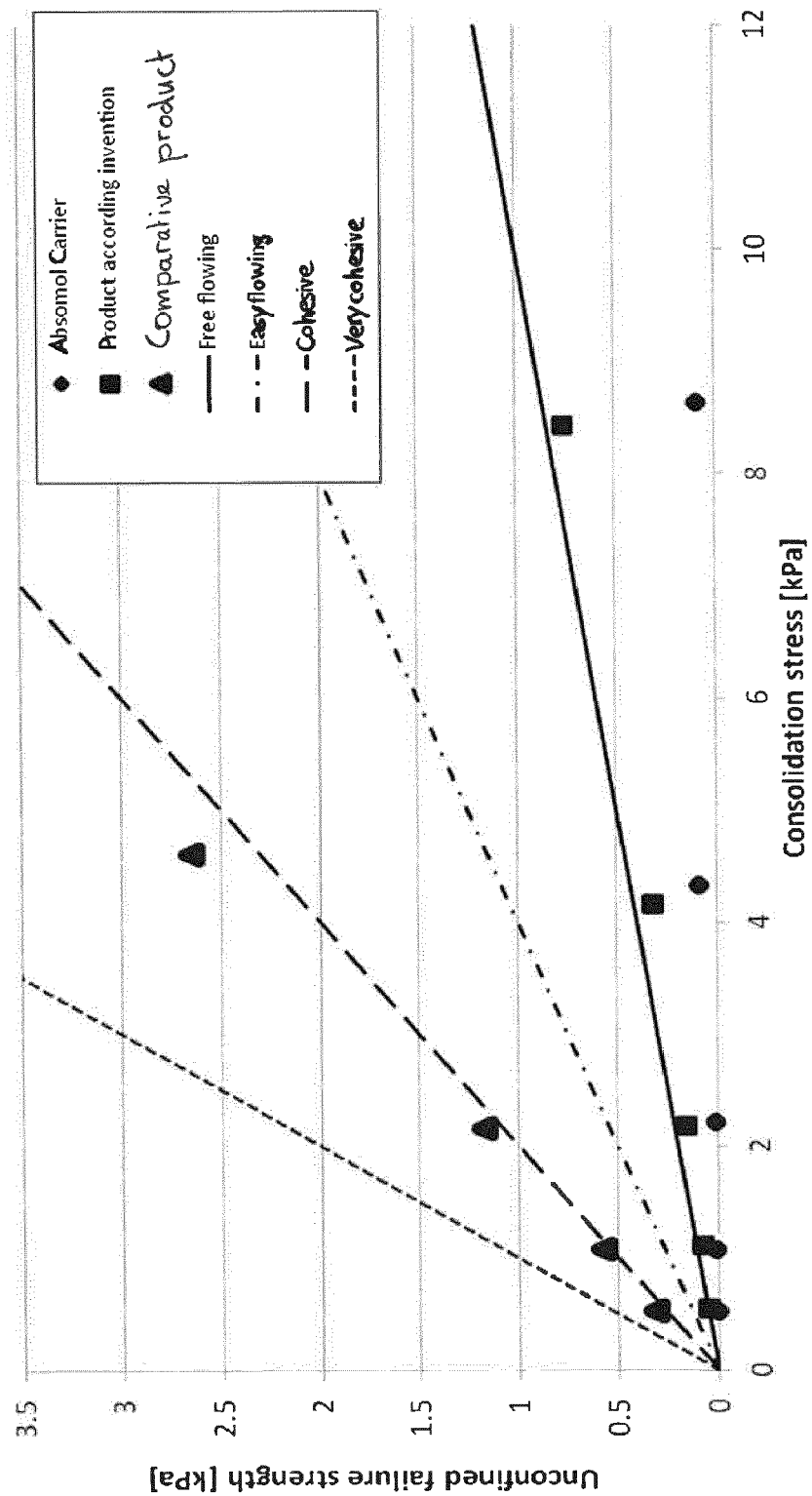

ACTIVE FORMULATION FOR USE IN FEED PRODUCTS

BACKGROUND

It is known in the art that hydroxyl-acid esters such as lactylates and related compounds may be attractive to include in feed products. For example, WO 2009/092787 describes the use of these compounds in the treatment or prevention of intestinal infections in animals, and to increase the animal growth rate.

A problem with these compounds, however, is to ensure that they are actually consumed by the animal in sufficient amounts. This requires that the product is mixed homogeneous through the animal feed, and that the mixture stays homogeneous upon transport and storage. Further, the presence of the specific active compound should not interfere with the processing of the feed, including its flow properties and storage properties. Obviously, the active compound should be incorporated in such a way that they are bioavailable, i.e., that they show the desired effect when eaten by the animal.

BRIEF SUMMARY

It has now been found that a product can be provided which solves these problems. The present invention pertains to a free-flowing particulate powder comprising 2-90 wt. % of an active compound on a carrier, wherein the carrier has a D(v,0.1) of at least 100 microns,
with the active compound being selected from
lactylate in accordance with formula 1, $$R2\text{-}COO\text{--}[\text{--}CH(CH_3)\text{--}COO]_n\text{--}R1 \qquad \text{Formula 1}$$

or a Na, K, Ca, Mg, Fe(II), Zn, NH$_4$, or Cu(II) salt thereof, a glycolylate of formula 2,

BRIEF DESCRIPTION OF THE DRAWING

The FIGURE is a graph showing the results of the critical flow function (fcc) of the powder according to the invention, the comparative powder, and the Absomol carrier.

DETAILED DESCRIPTION $$R2\text{-}COO\text{--}[\text{--}CH2\text{-}COO]_n\text{--}R1 \qquad \text{Formula 2,}$$

or a Na, K, Ca, Mg, Fe(II), Zn, NH$_4$, or Cu(II) salt thereof a lactate ester of formula 3, $$HO\text{--}CH(CH_3)\text{--}COO\text{--}R2 \qquad \text{Formula 3}$$

and/or a glycolic acid ester of formula 4, $$HO\text{--}CH2\text{-}COO\text{--}R2 \qquad \text{Formula 4}$$

wherein in the above formula R1 is selected from H, n stands for an integer with a value of 1-10, and R2 stands for a C1-C35 alkyl or alkenyl chain which may be branched or unbranched.

It is noted that WO2009/092787 indicates the possibility of combining the active compound with a support. The supports mentioned, however, are not suitable for the manufacture of free-flowing powders containing 10-90 wt. % of compound on a carrier. More in particular, some of the products mentioned therein, i.e., vegetable fiber material, cellulose, starch, gypsum, and lime, have insufficient absorption capacity to provide a free-flowing powder. For these materials, the product will be retained on the surface, resulting in a sticky non-free flowing material. The publication also mentions the use of silica, without specifying the further properties thereof. It has been found that where the compound is formulated with silica, a product may be obtained consisting of a core of active compound coated with the silica particles. These particles are not free-flowing and not stable under storage conditions.

The Particles

The present invention pertains to a free-flowing particulate powder comprising 2-90 wt. % of a specific active compound on a carrier, the carrier having a D(v,0.1) of at least 100 microns.

The powder according to the invention is free-flowing. In the context of the present invention, the indication free-flowing means that it has a Hausner ratio of at most 1.25, preferably lower as will be described below. It is preferred if the powder meets as many as possible of the further flowability parameters discussed below, which are all measures of the flowability under different conditions.

The Hausner ratio is the ratio between the packed bulk density and the aerated bulk density. The powder according to the invention has a Hausner ratio of at most 1.25. A powder with a Hausner ratio above this value is considered to have insufficient flow properties. Preferably, the Housner ratio is below 1.19, more preferably below 1.12. A powder with a Hausner ratio below 1.12 is considered a preferred embodiment of the present invention, as it has excellent flowing properties.

The packed bulk density and the aerated bulk density are determined using a Hosokawa powder tester according to standard test conditions. The aerated bulk density is obtained by dropping the sample through a vibrating chute to a fixed volume cup. The weight fluctuation is calculated and the result is displayed. The packed bulk density is obtained by tapping the sample a precise number of times from a standard height. A cup extension piece is fixed and powder is added, then the tapping process is started. At the end, the excess of powder is scraped and the filled cup is weighed on a balance.

The powder according to the invention preferably has an angle of repose of 45° or lower. The angle of repose is defined as the angle of the free surface of a heap of particulate material to the horizontal plane. It is a measure of the potential of the powder to flow. It is measured by carefully pouring the powder onto a flat surface using the Hosokawa powder tester. More preferably, the powder has an angle of repose of 40° or lower, in particular 35° or lower, in some embodiments even 30° or lower.

The powder according to the invention preferably has an angle of spatula of 45° or lower. The angle of spatula simulates the flowability of a powder when undergoing friction between the particles, e.g. when flowing from a hopper. Powder is deposited on the spatula to measure the first angle. The spatula undergoes a shock, upon which a second angle is formed. The angle of spatula is the average of the two angles. The measurement is carried out using the Hosokawa powder tester. More preferably, the powder has an angle of spatula of 38° or lower, in some embodiments even lower, such as 31° or lower.

The powder according to the invention may also be characterised through its fcc, which stands for critical flow function. It is a measure for the behaviour of the powder under stress or compression. The ffc is measured using Powder Flow Tester (PFT) (Brookfield PFT-400 with a Vane Lid). The principle of operation of the PFT is to drive a compression lid vertically downward into a powder sample contained in an annular shear cell. The powder sample has a defined volume and the weight of the sample is measured before starting the test. A calibrated beam load cell is used to control the compaction stress applied to the powder. The annular shear cell is then rotated at a defined speed and the torque resistance of the powder in the shear cell moving against the powder in the stationary lid is measured by a calibrated reaction torque sensor. The ffc is the ratio of the principal consolidation stress ($\sigma 1$) to the unconfined failure strength ($\sigma c$): ffc=$\sigma 1/\sigma c$.

In one embodiment, the powder according to the invention has an fcc at $\sigma 1=0.5$ kPa of at least 10, in particular at least 20. The fcc at $\sigma 1=0.5$ kPa may be much higher, e.g., at least 50.

In one embodiment, the powder according to the invention has an fcc at $\sigma 1=8$ kPa of at least 4, in particular at least 10. The fcc at $\sigma 1=8$ kPa may be much higher, e.g., at least 20 or at least 40.

It is preferred for the particles of the powder according to the invention to be not too small, because this will make them difficult to mix through feed components while still obtaining a stable mixture, i.e. a mixture that does not separate out under vibrations, transport or storage. This is ensured, int. al, by using a carrier with a D(v,0.1) of at least 100 microns.

In one embodiment, the powder has a D(v,0.1) of at least 100 microns, in particular at least 150 microns, more in particular at least 200 microns.

It is preferred for the powder according to the invention not to be too large, because this may again lead to segregation problems. In one embodiment, the powder has a D(v,0.9) of at most 1200 microns, in particular at most 1000 microns, more in particular at most 900 microns.

In one embodiment, the powder according to the invention has a D(v,0.5) of between 300 and 800 microns, in particular between 400 and 600 microns.

In the above, D(v,0.1) means that 10% of the volume distribution is below this value. D(v,0.9) means that 90% of the volume distribution is below this value. D(v,0.5) is the diameter where 50 vol. % of the distribution is above and 50% is below this value. This value is also indicated as the volume median diameter.

It may be preferred for the powder according to the invention to have a relatively narrow particle size distribution, as this may be beneficial to the stability of the product. This can be expressed as the span, which is defined as (D(v,0.9)-D(v,0.1))/D(v,0.5). In one embodiment, the powder has a span of 0.8-1.2, in particular 0.9-1.1.

The particle size distribution is determined using a Malvern Mastersizer 2000 (size ranges from 0.02 μm to 2000 μm, dispersive air pressure ranges 0-4 bar). The below listed parameters are fixed at starting point.
 Control Software: Scirocco 2000, Laser diffraction
 Pressure: 0.5 bar
 Vibration: 75%
 Time: 10 s.
 SOP: PSD 0.5 bar (auto duplo)
 Powder feeder: 4 mm
 Amount of sample: 2 spatula of 5.3 cm2

The powder according to the present invention comprises 2-90 wt of the active compound. If the amount is below 2 wt. %, the efficacy of adding the active compound through the powder is generally too low. That is, the amount of active component provided per gram of powder is too low. When the amount of active component is above 90 wt. %, the amount of carrier will be below 10 wt. %. Such a low amount of carrier makes it difficult to prepare a free-flowing powder product according to the invention. Within the specified range, the amount of active compound preferably is as high as possible, e.g., at least 5 wt. %, more preferably at least 10 wt. %, still more preferably at least 20 wt. %, preferably at least 30 wt. %, at least 40 wt. %. In some embodiments, values of at least 60 wt. % may be obtained.

The amount of active compound that is provided is dependent on the properties of the carrier. Preferably, the amount will be selected such that at least 50% of the active compound is absorbed into the carrier pores, more preferably at least 70%, still more preferably at least 90%, even more preferably at least 95%. It is particularly preferred for all or essentially all of the active compound to be absorbed into the carrier pores, so that the surface of the carrier is kept tack-free and the flow properties of the powder are not affected. It is within the scope of the skilled person to determine the appropriate amount on a case by case basis.

In one embodiment of the present invention particles are used which are quite hard. For example, particles may be used with a hardness on the Mohs scale in the range of 1-3, e.g., diatomaceous earth particles which have a hardness of 1-2, or vermiculite particles which have a hardness of 2-3.

The powder of the present invention has good storage stability under practical conditions, where the powder, or a feed containing the powder, may encounter temperatures above ambient. In one embodiment, the powder shows, after heat treatment one or more of the preferred values for the Hausner ratio and the other flowability parameters discussed above.

If so desired, the particles may be provided with a coating to grant additional properties to the powder. In one embodiment the coating is a colouring material, e.g., a pigment. For example, a TiO2 coating may be used to provide a white particle. In another embodiment, the powder may be provided with a coating of a fatty acid or a biodegradable membrane, e.g., to reduce the risk of leaching of the active compound from the particles.

The Carrier

The carrier used in the present invention has a (v,0.1) of at least 100 microns. It has been found that this feature is essential to obtaining a free-flowing powder. Not wishing to be bound by theory is believed that this size is required to ensure that the active compound is impregnated into the carrier, instead of the carrier particles adhering to the surface of particles of the active compound. In the latter case, a free-flowing powder will not be obtained. Further, a powder will not be obtained which can withstand shear conditions, or which shows stability upon storage.

It may be preferred for the carrier to have a D(v,0.1) of at least at least 150 microns, more in particular at least 200 microns.

It may preferred for the carrier used in the invention not to be too large, because this may again lead to segregation problems. In one embodiment, the carrier has a D(v,0.9) of at most 1200 microns, in particular at most 1000 microns, more in particular at most 900 microns.

In one embodiment, the carrier has a D(v,0.5) of between 300 and 800 microns, in particular between 400 and 600 microns.

It may be preferred for the carrier to have a relatively narrow particle size distribution, as this may be beneficial to the stability of the product. This can be expressed as the span, which is defined as (D(v,0.9)-D(v,0.1))/D(v,0.5). In one embodiment, the powder has a span of 0.8-1.2, in particular 0.9-1.1.

The carrier has a particle size which is of the same range as that of the product particles, as defined above. It is a particular feature of the present invention that this is the case. The same preferred ranges apply.

The carrier meets the same flowability requirements as the product. The same preferred ranges apply.

In one embodiment, the carrier has a bulk density of at least 0.1 ml/g, in particular at least 0.2 g/ml, more in particular at least 0.35 g/ml. In one embodiment, a material, e.g., diatomaceous earth is used with a bulk density of at least 0.45 g/ml. In some embodiments a material may be used which has a bulk density which is even higher, e.g., at least 0.65 g/ml.

A surprising aspect of the present invention is that it has appeared that even though the active compound is present in the pores of a carrier material, it still shows bioactive effects comparable to the provision of the active compound as such.

In one embodiment, the carrier has a surface area, as determined through BET of at least 10 m2/g, in particular at least 20 m2/g. The surface area is a measure for the porosity of the particle.

In one embodiment, the carrier has a pore volume of at least 0.1 ml/g, in particular at least 0.2 ml/g. In some embodiments, the pore volume is at least 0.4 ml/g, or at least 0.6 ml/g, or even at least 0.75 ml/g. As a general maximum, a value of 1.5 ml/g may be mentioned. Large pore volumes are considered preferred, because it is expected that they will be accompanied by higher possible loadings.

In one embodiment, the carrier used in the present invention is a powder of a porous inorganic oxide. Examples of suitable inorganic porous oxide powders are powders comprising oxides of one or more of Al, Si, Mg, Ti, Fe, Ca, K, Na. Examples include powders comprising alumina, silica, titania, diatomaceous earth, and clays, e.g., smectite clays such as vermiculite or sepiolite, and anionic clays such as hydrotalcite.

In one embodiment the use of diatomaceous earth is considered preferred, as it combines high strength with good loadability.

In another embodiment, the use of vermiculite is preferred, as it has shown a high loading ratio.

In another embodiment the use of sepiolite is preferred, because it combines high loadability with high bulk density, allowing a high mass in low volume.

In another embodiment, the carrier used in the present invention is an organic porous material, e.g., expanded starch-containing particles. Expanded starch-containing particles are known in the art. They can be manufactured in numerous ways, in al. by extruding starch-containing raw material at increased temperature. A starch-containing raw material suitable for extrusion may be manufactured by grinding starch containing matter such as corn and wheat with water, stream, or a water-containing material such as fruit or vegetables to form a paste. In one embodiment expanded organic particles are used with contain expanded starch and also other compounds attractive for use in feed products.

For preferred embodiments for the surface area, bulk density and pore volume reference of the organic particles, e.g., expanded starch-containing particles, reference is made to what is stated above. For the particle size it is noted that expanded starch particles as sold may be larger than indicated above. Depending on the end use, they may be grinded before contacting them with the active compound. Depending on the application, it may sometimes be attractive to use relatively large particles, e.g., in feed for larger animals. It is within the scope of the skilled person to determine a suitable particle size in this respect. It is noted that for larger particles the use of organic porous materials, in particular expanded starch is particularly attractive, because the acceptability of organic particles of this size to the animal may be better than for inorganic particles.

The Active Compound

In the present invention, use may be made of an active compound selected from one or more of a lactylate in accordance with formula 1, or a Na, K, Ca, Mg, Fe(II), Zn, $NH_4$, or Cu(II) salt thereof, a glycolylate of formula 2, or a Na, K, Ca, Mg, Fe(II), Zn, $NH_4$, or Cu(II) salt thereof, a lactate ester of formula 3, and/or a glycolic acid ester of formula 4.

The use of a lactylate of formula 1 or a salt thereof has been found to be preferred.

In a preferred embodiment of the present invention, R2 is an alkyl or alkenyl chain with 6-20 carbon atoms. More in particular, R2 is an alkyl or alkenyl chain with 6-18 carbon atoms. In this embodiment, suitable substituents include groups with 6 carbon atoms (capronic), 8 carbon atoms (caprylic) 10 carbon atoms (capric acid), 12 carbon atoms (lauryl), 14 carbon atoms (myristyl), 16 carbon atoms (cetyl, palmityl), 18 carbon atoms (stearyl). Mixtures of two or more compounds may also be used. Where a salt is used, the use of a Na, K, Ca, or Mg salt may be particularly preferred.

The value for n is preferably in the range of 1-5. More in particular n has a value of 1, 2, or 3.

The use of lauroyl lactylate, myristolyl lactylate, and their sodium salts is particularly preferred. In one embodiment, a mixture is used comprising 5-95 wt. % of lauroyl lactylate and 95-5 wt. % of myristoyl lactylate, or the sodium salt(s) of these compounds are used, more in particular, a mixture is used comprising 25-75 wt. %, more in particular 40-60 wt. % of lauroyl lactylate, and 75-25 wt. %, more in particular 40-60 wt. % of myristoyl lactylate, or the sodium salt(s) of these compounds.

The active compound used in the present invention is attractive for use in animal feeds. It shows, e.g., antibacterial activity. E.g., WO 2009/092787 describes the use of these compounds in the treatment or prevention of intestinal infections in animals, and to increase the animal growth rate.

Particle Manufacture

The powder according to the invention may be manufactured by contacting the active compound in the liquid form with the carrier. Due to the carrier being porous, the active compound will be absorbed into the pores of the carrier, resulting in an impregnated particle.

The active compound is in the liquid form when it is applied onto the carrier. Preferably, this is effected by ensuring that the active compound is at a temperature above its melting point. If so desired it is possible to a have a solvent present in the liquid active compound, e.g. to help dissolve the compound or to decrease the viscosity of the liquid. As the presence of solvent may decrease the amount of active compound that may be adsorbed into the carrier, it may be preferred to use only a low amount of solvent, if solvent is used at all. Preferably, the liquid has a viscosity of at most 250 cP to increase processing properties, in particular at most 200 cP, more in particular at most 150 cP. (viscosity determined with a constant shear rate of 10 l/s, a two-step temperature profile of 140° C.→50° C. and 50° C.→140° C., duration 20 minutes and 1 hour).

For the lactylates of formula 1, in particular C6-C18 lactylates as described above it is preferred for the impregnation solution to be at a temperature of at least 120° C., because this will ensure an adequate viscosity of the mixture. Working at a temperature above 140° C. may be particularly preferred. The upper limit of the solution temperature is not critical as long as the product does not degrade at the selected temperature. Generally, the temperature of the liquid will be at most 200° C.

In a preferred embodiment, the contacting of the active compound in the liquid form with the carrier is carried out under reduced pressure, e.g., at a pressure below 800 mbar, more in particular below 500 mbar. In one embodiment, the contacting takes place at a pressure between 50 and 200 mbar.

The contacting may be carried out in manners known in the art, e.g., by spraying the active compound over a fluidised bed of carrier particles.

It may be preferred to heat the carrier particles to such a temperature that the active compound does not immediately solidify on the surface, to prevent the active compound from solidifying on the surface of the particles, and this may detrimentally affect the flow properties of the powder. For example, the carrier may be brought to a temperature of at least 80° C., in particular at least 100° C. As a maximum value a value of 250° C. may be mentioned.

Animal Nutrition Composition Comprising the Powder

The free-flowing powder according to the invention may be administered to animals as a component of a conventional solid animal feed composition. The composition may also be administered to the animal in a separate step, independent from the provision of a conventional animal feed composition.

The amount of the powder according to the invention that is incorporated into a feed composition is suitably in the range from 0.0001-5%, calculated as active component, based on the total weight of each feed fed to the animal. In a preferred embodiment, the amount may be in the range of 0.001 to 2%, based on the total weight of each feed fed to the animal. In one embodiment of the present invention the amount may be in the range of 0.001 to 1 wt. %, more in particular 0.001 to 0.5 wt. %, based on the total weight of each feed fed to the animal. It is within the scope of the skilled person to determine the amount necessary.

As mentioned above, the active compound may be administered to animals as a component of a conventional animal feed composition. Depending on the animal to be treated, a conventional animal feed composition may comprise one or more of wheat, starch, meat and bone meal, maize, sunflower meal, corn, cereals, barley, soybean meal, tapioca, citrus pulp, legumes, beet pulp, etcetera. It is within the scope of the skilled person to determine the composition of a suitable feed product.

In one embodiment, the powder according to the invention is first incorporated into a premix comprising one or more of vitamins and nutrients, and the premix is then incorporated into the animal feed. Depending on the further composition, the premix may contain, e.g., 60-90 wt. % of powder according to the invention, 15 up to 60 wt. % of powder according to the invention, or 5 up to 15 wt. % of powder according to the invention.

The invention thus also pertains to an animal nutrition composition, comprising the powder as described above, and at least one further nutritious component. The animal nutrition composition may, e.g., be a feed or a premix as described above. The invention also pertains to the use of the powder in an animal nutrition composition.

The powder of the present invention is suitable, in al., for treating or preventing of infections in animals, in particular intestinal infections, in particular intestinal infections caused by gram-positive bacteria. The powder according to the invention is of particular interest in the prevention and treatment of intestinal infections by *Clostridia*. In one embodiment, the powder according to the invention is used in the prevention or treatment of intestinal infections caused by *Clostridium*, in particular by *Clostridium perfringens* in poultry, in particular in chicken. The powder of the present invention is also suitable for increasing the growth of an animal.

The present invention thus also pertains to a method for preventing or treating intestinal infections caused by gram-positive bacteria in animals, and/or increasing the growth of the animal, comprising feeding the animal with an effective amount of the powder as described herein.

For details on the animals that may be treated and the bacteria the growth of which may be prevented, reference is may to WO2009/092787, the relevant parts of which are incorporated herein by reference.

The present invention will be elucidated by the following examples, without being limited thereto or thereby.

EXAMPLE 1

Powder Based on Diatomaceous Earth Carrier

The starting material was 4.65 kg of calcined diatomaceous earth (Absomol AB-10 KF provided by Damolin s.a), the particle size distribution of which is given in the following table:

| Sample Name | D (0.1) μm | D (0.5) μm | D (0.9) μm | D [3,2] μm | D [4,3] μm | Span (—) |
|---|---|---|---|---|---|---|
| Absomol AB10KF | 278 | 471 | 764 | 432 | 499 | 1.03 |

4.65 kg of this material was heated to a temperature of 100° C. and brought to a vacuum pressure of 200 mbara. Then it was sprayed with 3.1 kg of PURAMIX 100 melt, which is a mixture of 70% wt sodium lauroyl lactylate and 30% wt sodium myristoyl lactylate at a nozzle pressure of 5 bar, a temperature of the liquid of 135 C and a spay rate of 7.5 kg/minute through a pressure nozzle. The end product had a temperature of 90° C. and a loading of 40 wt. %. It was a free-flowing powder (Hausner ratio of 1.04) with a non-sticky (tack-free) surface. The final product showed the same particle size characteristics and flowability characteristics as the initial carrier, indicating that the liquid has been absorbed by the particles.

EXAMPLE 2

Powder Based on Vermiculite Carrier

The starting material was Vermiculite Nr.0 exfoliated (provided by KRAMER PROGETHA), the particle size distribution of which is given in the following table:

| Sample Name | D (0.1) μm | D (0.5) μm | D (0.9) μm | D [3,2] μm | D [4,3] μm | Span (—) |
|---|---|---|---|---|---|---|
| Vermiculite expanded nr. 0 | 296 | 525 | 955 | 455 | 585 | 1.25 |

1.3 kg of starting material was heated to a temperature of 100° C. and brought to a vacuum pressure of 200 mbara. Then it was sprayed with 1.95kg of PURAMIX 100 melt, which is a mixture of 70% wt sodium lauroyl lactylate and 30% wt sodium myristoyl lactylate at a nozzle pressure of 5 bar, a temperature of the liquid of 135C and a spay rate of 2.6 kg/minute through a pressure nozzle. The end product had a temperature of 95° C. and a loading of 60 wt. %. It was a free-flowing powder (Hausner ratio of 1.07) with a non-sticky (tack-free) surface. The final product showed the same particle size characteristics and flowability characteristics as the initial carrier, indicating that the liquid has been absorbed by the particles.

EXAMPLE 3

Powder Based on Sepiolite Carrier

The starting material was Sepiolite (Provided by Provimi B. V Netherlands), the particle size distribution of which is given in the following table:

| Sample Name | D (0.1) μm | D (0.5) μm | D (0.9) μm | D [3,2] μm | D [4,3] μm | Span (—) |
|---|---|---|---|---|---|---|
| Sepiolite | 178 | 365 | 651 | 205 | 389 | 1.30 |

7.3 kg of starting material was heated to a temperature of 100° C. and brought to a vacuum pressure of 200 mbara. Then it was sprayed with 3.2 kg of PURAMIX 100 melt, which is a mixture of 70% wt sodium lauroyl lactylate and 30% wt sodium myristoyl lactylate at a nozzle pressure of 5 bar, a temperature of the liquid of 135 C and a spay rate of 2.6 kg/minute through a pressure nozzle. The end product had a temperature of 80° C. and a loading of 30 wt. %. It was a free-flowing powder (Hausner ratio of 1.03) with a non-sticky (tack-free) surface. The final product showed the similar size characteristics and flowability characteristics as the initial carrier, indicating that the liquid has been absorbed by the particles.

EXAMPLE 4

Flow Function Measurement of Product According to the Invention and Comparative Product A product according to the invention was prepared using PURAMIX 100 on a diatomaceous earth as described in Example 1. The product contained 40 wt. % of active compound on the carrier.

A comparative product was manufactured by melting 60 wt. % of PURAMIX 100 and mixing it with 40 wt. % stearic acid. The melt was allowed to cool, further chilled with liquid nitrogen, and ground using a laboratory grinder. The produced particles were mixed with 2 wt. % of silica as flow improvement agent. The silica was Sipernat 22S, with a particle size of 11.5 microns (d50, laser diffraction in accordance with ISO 13320-1)

The product has the following particle size distribution:

| Sample Name | D (0.1) μm | D (0.5) μm | D (0.9) μm | D [3,2] μm | D [4,3] μm | Span (—) |
|---|---|---|---|---|---|---|
| PURAMIX 100/ Stearic Acid 60/40 + 2% silica | 119 | 614 | 1324 | 176 | 677 | 1.96 |

The critical flow function (fcc) of the powder according to the invention, the comparative powder, and the Absomol carrier were determined. The fcc is a measure for the behaviour of the powder under stress or compression, and has been discussed earlier. The results are presented in the FIG. 1.

As can be seen from the FIG. 1, the product according to the invention is free-flowing; almost as good as the carrier itself. On the other hand, the comparative product is cohesive/very cohesive.

EXAMPLE 5

Use of an Organic Porous Carrier

A carrier was prepared by grinding corn and wheat, adding steam, and extruding at increased temperature through an extruder to form expanded starch-containing particles with a diameter of 2 mm. The extrudates were allowed to dry.

The material was heated to a temperature of 100° C. and brought to a vacuum pressure of 200 mbara. Then it was sprayed with PURAMIX 100 melt, which is a mixture of 70% wt sodium lauroyl lactylate and 30% wt sodium myristoyl lactylate at a nozzle pressure of 5 bar, a temperature of the liquid of 135 C and a spay rate of 7.5 kg/minute through a pressure nozzle. The end product had a temperature of 90° C. and a loading of 40 wt. %. The particles were not sticky and free-flowing, indicating that the liquid had been absorbed by the particles.

EXAMPLE 6

Powder Based on Organic Carrier

The carrier prepared in Example 5 was ground too form a powder. The powder was impregnated using the same processing conditions as described in Example 5. The loading of the final product was 20 wt. %. The final powder was free-flowing, and non-sticky.

The invention claimed is:

1. Free-flowing particulate powder comprising 10-90 wt. % of an active compound on a porous carrier and having a Hausner ratio of at most 1.25, wherein:
   the carrier has a D(v, 0.1) of at least 100 microns and a D(v, 0.5) of between 300 and 800 microns;
   pores of said porous carrier are impregnated with an amount of active compound that has solidified therein; and
   the active compound is selected from:
      lactylate in accordance with formula 1, R2-COO—[—CH(CH$_3$)—COO]$_n$—R1     Formula 1 or a Na, K, Ca, Mg, Fe(II), Zn, NH or Cu(II) salt thereof,
      a glycolylate of formula 2, R2-COO—[—CH$_2$—COO]$_n$—R1     Formula 2 or a Na, K, Ca, Mg, Fe(II), Zn, NH4, or Cu(II) salt thereof,
      a lactate ester of formula 3, HO—CH(CH$_3$)—COO—R2     Formula 3 and/or
      a glycolic acid ester of formula 4,

HO—CH$_2$—COO—R2     Formula 4 wherein in the above formulae:
      R1 is selected from H,
      n stands for an integer with a value of 1-10, and
      R2 stands for a C1-C35 alkyl or alkenyl chain which may be branched or unbranched.

2. The powder according to claim 1, which comprises at least 20 wt. % of the active compound.

3. The powder according to claim 1, wherein the carrier has a surface area, as determined through BET, of at least 10 m²/g.

4. The powder according to claim 1, wherein the carrier has a pore volume of from 0.1 to 1.5 ml/g.

5. The powder according to claim 1, wherein the carrier has a bulk density of at least 0.1 g/ml.

6. The powder according to claim 1, wherein the carrier is a porous inorganic oxide.

7. The powder according to claim 6, wherein the carrier is a powder comprising one or more of alumina, silica, titania, diatomaceous earth, and clays.

8. The powder according to claim 7, wherein the clays are selected from smectite clays and anionic clays.

9. The powder according to claim 7, wherein the carrier is a powder comprising diatomaceous earth, sepiolite, or vermiculite.

10. The powder according to claim 1, wherein the carrier is an organic porous material.

11. The powder according to claim 1, wherein the active compound is a lactylate of formula 1 or a salt thereof.

12. The powder according to claim 11, wherein the active compound is selected from lauroyl lactylate, myristolyl lactylate, and their sodium salts.

13. A method for manufacturing the powder according to claim 1, comprising a step of contacting the active compound in liquid form with the carrier.

14. The method according to claim 13, wherein the step of contacting the active compound in liquid form with the carrier is carried out under reduced pressure.

15. An animal nutrition composition comprising the powder according to claim 1 and at least one further nutritious component.

16. A method for increasing growth of an animal, comprising feeding the animal an effective amount of the powder of claim 1.

17. The powder according to claim 1, wherein the carrier has a pore volume of from 0.4 to 1.5 ml/g.

\* \* \* \* \*